US012637645B2

(12) United States Patent
D'Apuzzo et al.

(10) Patent No.: US 12,637,645 B2
(45) Date of Patent: May 26, 2026

(54) DEFORMABILITY OF A CELL RESPONSIVE TO A PRESSURE WAVE

(71) Applicant: Hewlett-Packard Development Company, L.P., Spring, TX (US)

(72) Inventors: Fausto D'Apuzzo, Palo Alto, CA (US); Viktor Shkolnikov, Palo Alto, CA (US); Alexander Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 735 days.

(21) Appl. No.: 18/012,613

(22) PCT Filed: Jul. 8, 2020

(86) PCT No.: PCT/US2020/041235
§ 371 (c)(1),
(2) Date: Dec. 22, 2022

(87) PCT Pub. No.: WO2022/010474
PCT Pub. Date: Jan. 13, 2022

(65) Prior Publication Data
US 2023/0250378 A1     Aug. 10, 2023

(51) Int. Cl.
*C12M 3/06*          (2006.01)
*C12M 1/34*          (2006.01)
(Continued)

(52) U.S. Cl.
CPC ............ *C12M 23/16* (2013.01); *C12M 35/04* (2013.01); *C12M 41/40* (2013.01);
(Continued)

(58) Field of Classification Search
CPC ........... B01L 3/50273; B01L 3/502761; B01L 2300/0816; B01L 2400/0415;
(Continued)

(56) References Cited

U.S. PATENT DOCUMENTS

| | | | |
|---|---|---|---|
| 6,067,859 A | 5/2000 | Kas et al. | |
| 2004/0106189 A1 | 6/2004 | Dodgson et al. | |

(Continued)

FOREIGN PATENT DOCUMENTS

| | | | | |
|---|---|---|---|---|
| CN | 107075431 A | * | 8/2017 | ......... F16K 99/0055 |
| KR | 10-2016-0139605 A | | 12/2016 | |

(Continued)

OTHER PUBLICATIONS

Machine Translation of KR-102119977-A1 (Year: 2025).*
Machine Translation of CN 107075431 A (Year: 2025).*

*Primary Examiner* — Michael L Hobbs
(74) *Attorney, Agent, or Firm* — Foley & Lardner LLP

(57) ABSTRACT

An example method for measuring deformability of a cell responsive to a pressure wave, consistent with the present disclosure, includes moving a cell of a sample into a cell probing chamber of a microfluidic device. While the cell is in the cell probing chamber, the method includes generating a pressure wave within the cell probing chamber by actuating a fluidic pump. The method further includes determining a deformability of the cell responsive to the pressure wave, using an imaging array synchronized with the actuation of the fluidic pump.

7 Claims, 15 Drawing Sheets

(51) Int. Cl.

| | |
|---|---|
| *C12M 1/42* | (2006.01) |
| *G01N 15/14* | (2006.01) |
| *G01N 15/1433* | (2024.01) |
| *G01N 15/10* | (2006.01) |

(52) U.S. Cl.
CPC ..... *G01N 15/1433* (2024.01); *G01N 15/1459* (2013.01); *G01N 2015/1006* (2013.01); *G01N 2015/1495* (2013.01)

(58) Field of Classification Search
CPC ...... C12M 23/16; C12M 35/04; C12M 41/10; G01N 15/1433; G01N 15/1459; G01N 15/147; G01N 2015/1006; G01N 2015/1495; G01N 27/44704; F04B 19/006
See application file for complete search history.

(56) References Cited

U.S. PATENT DOCUMENTS

| | | | |
|---|---|---|---|
| 2007/0243523 A1* | 10/2007 | Ionescu-Zanetti | ........................... G01N 15/1459 977/924 |
| 2008/0240539 A1* | 10/2008 | George | ................. G01N 21/47 382/133 |
| 2014/0087412 A1* | 3/2014 | Fouras | .................. G01N 11/00 435/287.1 |
| 2018/0008979 A1 | 1/2018 | Yu et al. | |
| 2018/0369816 A1 | 12/2018 | Al et al. | |

FOREIGN PATENT DOCUMENTS

| | | |
|---|---|---|
| KR | 10-2017-0123832 A | 11/2017 |
| KR | 10-2119977 B1 | 6/2020 |
| WO | 2020/032970 A1 | 2/2020 |

\* cited by examiner

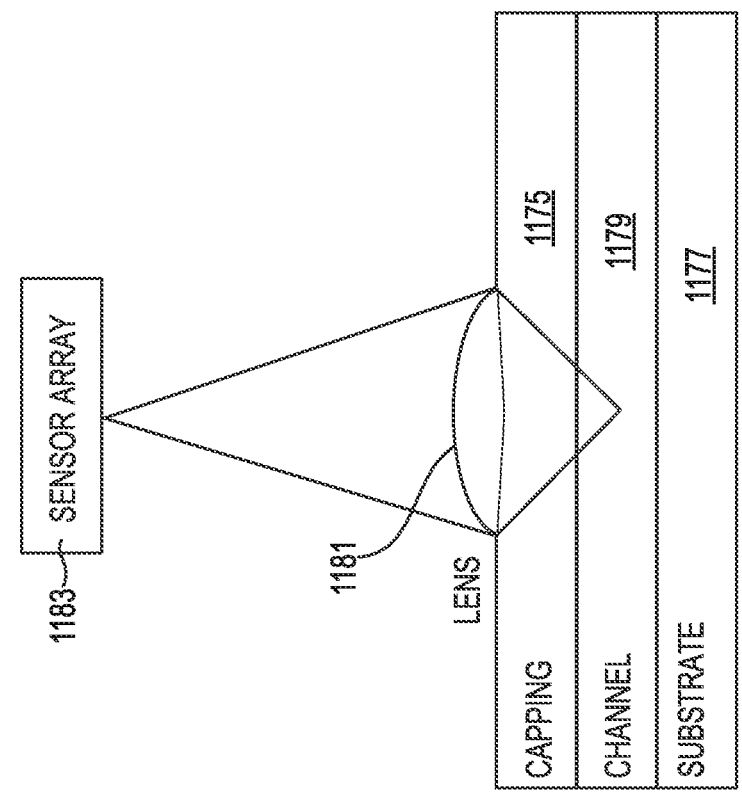
1183 — SENSOR ARRAY
1181 — LENS
1175
1179
1177
CAPPING
CHANNEL
SUBSTRATE
FIG. 11
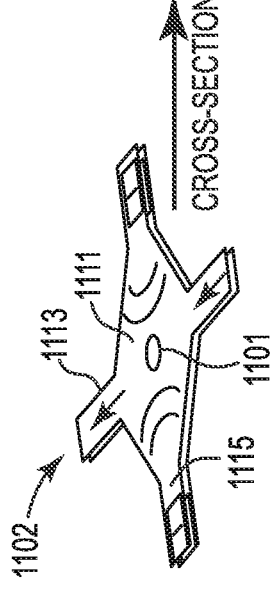
1102
1113
1111
1101
1115
CROSS-SECTION

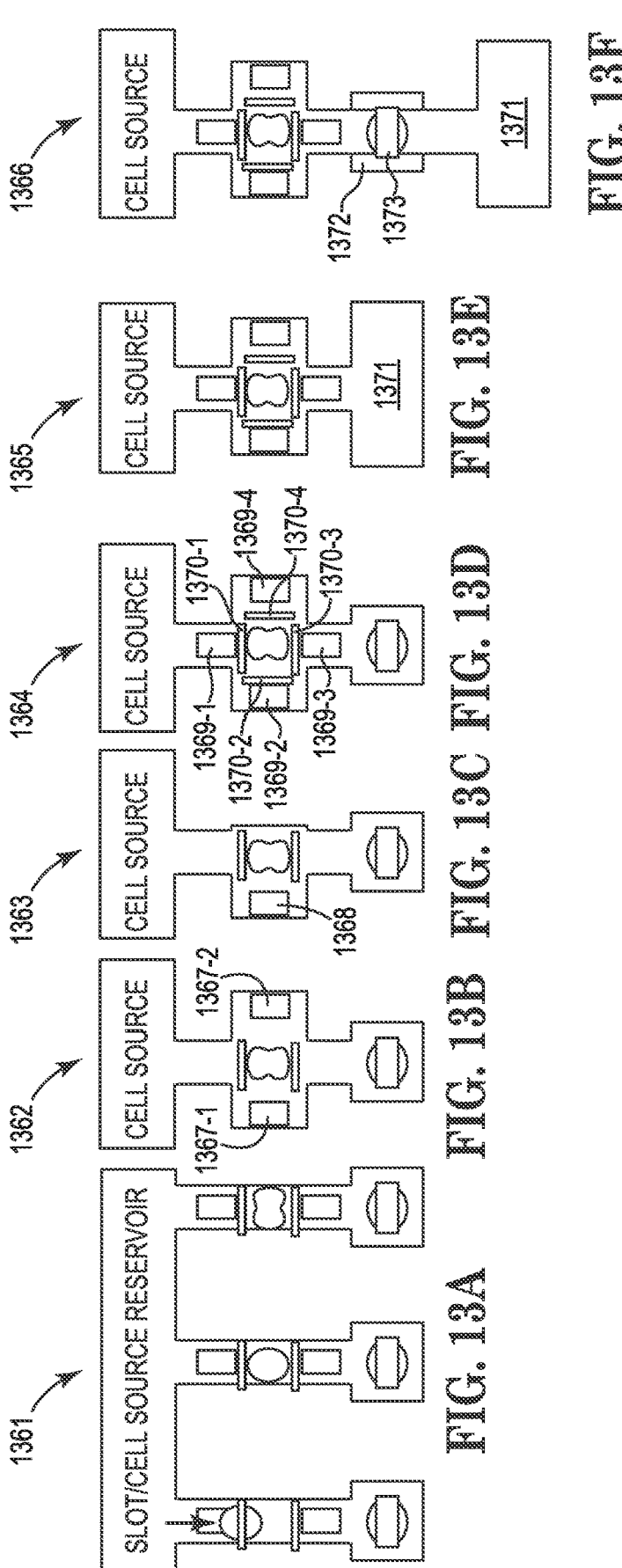

DEFORMABILITY OF A CELL RESPONSIVE TO A PRESSURE WAVE

CROSS-REFERENCE TO RELATED APPLICATIONS

This application is a National Stage Patent Application of PCT/US2020/041235, filed Jul. 8, 2020, which is hereby incorporated by reference in its entirety.

BACKGROUND

Cellular mechanical properties may be indicative of various disease states. For example, a change in the deformability of red blood cells is an early indication of sepsis as well as hereditary disorders such as spherocytosis, elliptocytosis, ovalocytosis, and stomatocytosis, metabolic disorders such as diabetes, hypercholesterolemia, and obesity, as well as other disorders such as adenosine triphosphate-induced membrane changes, oxidative stress, and paroxysmal nocturnal hemoglobinuria. A change in red blood cell deformability is also associated with malaria, sickle cell anemia, and myocardial infarction. As a further example, change in deformability of white blood cells has also been associated with sepsis.

Rheological phenotyping, or the characterization of the deformability of cells, allows for detection of various diseases. In cancer research, elasticity of circulating tumor cells is strongly correlated with the metastatic potential of the cells, with more elastic cells having higher metastatic potential.

BRIEF DESCRIPTION OF THE DRAWINGS

FIG. 11 illustrates an example apparatus for measuring deformability of a cell responsive to a pressure wave, consistent with the present disclosure.

FIGS. 13A, 13B, 13C, 13D, 13E, and 13F illustrate a variety of different apparatuses for measuring deformability of a cell responsive to a pressure wave, consistent with the present disclosure.

DETAILED DESCRIPTION

Figure 1:
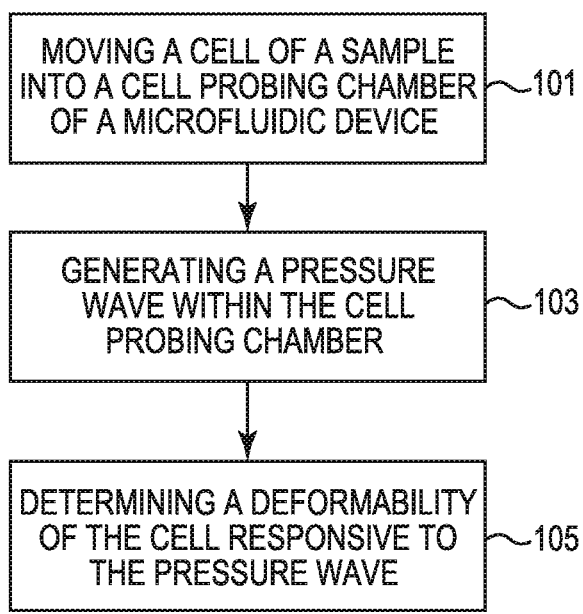
FIG. 1 illustrates an example method for measuring deformability of a cell responsive to a pressure wave, consistent with the present disclosure.

In the following detailed description, reference is made to the accompanying drawings which form a part hereof, and in which is shown by way of illustration specific examples in which the disclosure may be practiced. It is to be understood that other examples may be utilized, and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

Biological cells are the basic building blocks of skin, tissues, and other materials. Cells and their organelles are enveloped by thin membranes that separate their chemical contents from the extracellular environment. Biological membranes are supramolecular assemblies composed of a lipid double layer with embedded and adsorbed membrane proteins. Each monolayer of the membrane consists of billions of adjacent lipid molecules, which are composed of two hydrophobic tails and a hydrophilic headgroup. The two monolayers taken together, facing each other with the hydrophobic tails, serve as a barrier of 4-10 nm thickness, which exhibits a partial permeability to some small hydrophobic and polar molecules.

Cell deformation and mechanical property analysis may allow for rheological phenotyping. For instance, cells may be brought into an apparatus and deformed. The flow may be driven by external pumps, and the deformation of the cell may be observed via a high-speed camera. The deformation is obtained later by post-processing. Post-processing of a large number of optical images takes a significant amount of time. Moreover, these devices are not able to sort the cells, as they cannot operate in real time. Furthermore, these devices take hours to process a large amount of cells (such as greater than $10^6$ cells) and are poorly amenable to point-of-care instrument solutions.

Deformability of a cell responsive to a pressure wave, consistent with examples of the present disclosure, may include moving a cell of a sample into a cell probing chamber of a microfluidic device, and while the cell is in the cell probing chamber, generating a pressure wave within the cell probing chamber by actuating a fluidic pump. By applying a pressure wave to the cell within the cell probing chamber, and determining the deformability of the cell responsive to the pressure wave, the deformability of the cell may be measured quickly and in parallel, such that a large number of cells may be processed simultaneously. For instance, in accordance with examples of the present disclosure, the deformability of thousands of cells may be determined simultaneously, as opposed to other systems that process a single cell at a time.

An example method for measuring deformability of a cell responsive to a pressure wave, consistent with the present disclosure, includes moving a cell of a sample into a cell probing chamber of a microfluidic device. The method includes generating a pressure wave within the cell probing chamber by actuating a fluidic pump while the cell is in the cell probing chamber. The deformability of the cell is determined responsive to the pressure wave, using an imaging array synchronized with the actuation of the fluidic pump.

In additional examples of the present disclosure, an apparatus for measuring deformability of a cell responsive to a pressure wave includes a cell source reservoir, a cell probing chamber fluidically coupled to the cell source reservoir, and a controller communicatively coupled to the cell probing chamber. The cell probing chamber includes a fluidic pump to move a single cell of a sample from the cell source reservoir to the cell probing chamber, and a sensor communicatively coupled to the fluidic pump. The sensor may detect a position of the cell within the cell probing chamber. The controller includes instructions to actuate the fluidic pump to generate a pressure wave within the cell probing chamber, and determine a deformability of the cell responsive to the pressure wave.

In yet a further example, an apparatus for measuring the deformability of a cell responsive to a pressure wave, consistent with the present disclosure, includes a cell source reservoir, a cell probing chamber fluidically coupled to the cell source reservoir, and a controller communicatively coupled to the fluidic pump and the resistor. The cell probing chamber includes a fluidic pump to move a single cell of a sample from the cell source reservoir to the cell probing chamber, and a resistor to generate a pressure wave within the cell probing chamber. The controller includes instructions to actuate the fluidic pump to move a cell from the cell source reservoir into the cell probing chamber, actuate the resistor to generate a pressure wave within the cell probing chamber, and determine a deformability of the cell responsive to the pressure wave.

Turning now to the Figures, FIG. 1 illustrates an example method 100 for measuring deformability of a cell responsive to a pressure wave, consistent with the present disclosure. At 101, the method 100 includes moving a cell of a sample into a cell probing chamber of a microfluidic device. As discussed further herein, flow within the microfluidic device may be controlled using a plurality of pumps, and an imaging array may be used to visualize cells within the microfluidic device. The fluid flow may be provided either on-chip or off-chip by pumps. As an example, the microfluidic device may include a plurality of resistors and a controller communicatively coupled to the plurality of resistors. In such examples, the method 100 may include using the controller communicatively coupled to the plurality of resistors, to selectively actuate a resistor of the plurality of resistors, or the plurality of resistors, to position the cell between the plurality of resistors. Examples are not so limited, however, and the method 100 may include performing rheological phenotyping of cells in a continuous or semi-continuous manner.

At 103, the method 100 includes generating a pressure wave within the cell probing chamber by actuating a fluidic pump while the cell is in the cell probing chamber. In various examples, the fluidic pump includes a plurality of resistors disposed within the cell probing chamber. In such examples, the method includes moving the cell into the cell probing chamber by actuating a resistor of the plurality of resistors. For instance, high-frequency thermal inkjet (TIJ) actuators may be fired simultaneously at a specified frequency and with a specified amount of force to create a pressure wave in the chamber. As described herein, generating the pressure wave includes actuating the plurality of resistors at a specified frequency to generate a steam bubble at each respective resistor, each steam bubble forming at the specified frequency. Similarly, the method may include generating a plurality of pressure waves within the cell probing chamber by actuating the fluidic pump, where each of the plurality of pressure waves provides a step-wise application of pressure on the cell. As used herein, a step-wise application of pressure refers to or includes a series of pulses of the fluidic pump where each successive pulse applies a greater amount of pressure on the cell than the previous pulse.

At 105, the method 100 further includes determining a deformability of the cell responsive to the pressure wave, using an imaging array synchronized with the actuation of the fluidic pump. As discussed further herein, the microfluidic chip may include a transparent surface that allows imaging, such as by epi-illumination microscopy. The imaging array may be part of the microfluidic chip, or be provided as a separate component from the microfluidic chip.

The method may further include determining the deformability of the cell using a high speed imaging array or a stroboscopic imaging array. For instance, the method may include measuring the width and/or length of the cell before application of the pressure wave, and measuring the width and/or length of the cell during application of the pressure wave. In various examples, the method 100 may include releasing the cell from the cell probing chamber by asymmetrically activating a plurality of fluidic pumps in the microfluidic device, as discussed herein.

Figure 2:
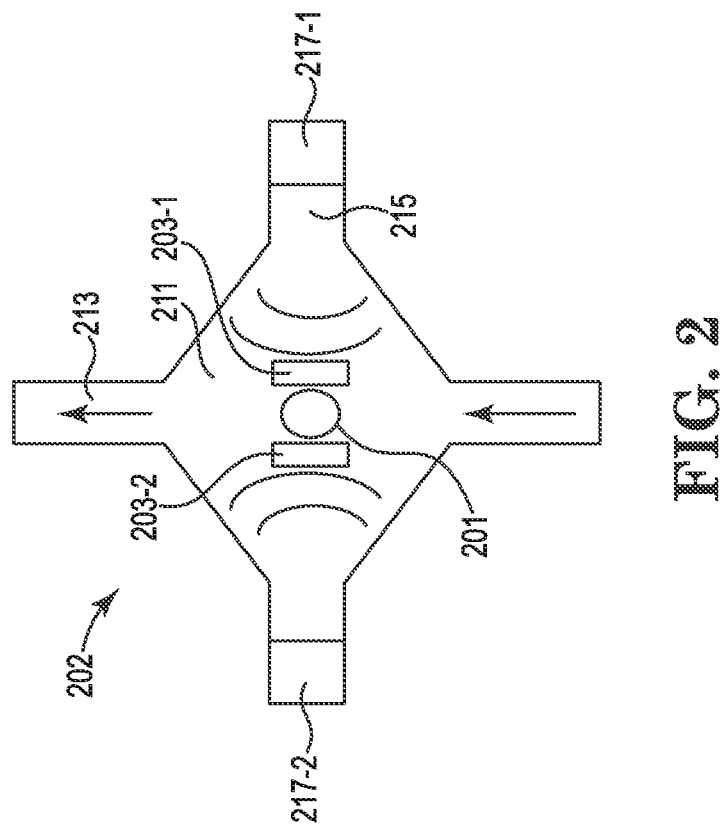
FIG. 2 illustrates an example apparatus for measuring deformability of a cell responsive to a pressure wave, consistent with the present disclosure.

FIG. 2 illustrates an example apparatus 202 for measuring deformability of a cell responsive to a pressure wave, consistent with the present disclosure. The apparatus 202 is capable of performing the method 100 illustrated in FIG. 1. For instance, the apparatus 202 is capable of moving a cell 201 of a sample into a cell probing chamber 211 of a microfluidic device 202. A sample, such as a biologic sample, may flow through channel 213 in the direction of the arrows. As discussed further herein, the fluid flow may be induced using internal pumps and/or external pumps. In some examples, the cell 201 may be isolated in the cell probing chamber 211 of the microfluidic chip 202 by terminating or reducing the flow of the biologic sample through the microfluidic chip 202. While complete flow termination may or may not be achieved, a significant reduction of the flow rate may enable additional time for deformation analysis to be performed. To detect positioning or isolation of a cell within the cell probing chamber 211, a sensor may be used. For instance, sensors 203-2 and 203-1 illustrated in FIG. 2 may detect presence of cell 201. Example sensors 203-2 and 203-1 may include impedance sensors, capacitance sensors, imaging sensors, or other types of sensors capable of detecting presence of a cell. The sensor measures the impedance of a fluid (e.g., a water based fluid carrying cells) within the microchannel analysis region.

Fluid may flow within channel 213 in a variety of ways, based on operation of an internal or external pump. In some examples, a pulsatory flow may be used to move cells through channel 213, rather than terminating or reducing the flow rate. For instance, an internal or an external pump may fire periodically and move cells through the cell probing chamber 211 in periodic waves. When the flow is produced by a pulsating pump such as an inertial pump, the flow rate per pulse of the inertial pump is well defined and cells are transported through the cell probing chamber 211 with precision steps.

Examples are not so limited, however, and deformation analysis may be performed without a change in the flow rate of the sample through channel 213. For instance, deformation analysis may be performed during continuous flow of the sample through channel 213. In such examples, positioning of a single cell within the cell probing chamber 211 is not used. Samples may be diluted and passed through channel 213, and through cell probing chamber 211 such that cells are passed through the cell probing chamber 211 one-by-one and imaged via the imaging array at a synchronized rate with a firing rate of actuators 217-1 and 217-2.

As discussed with regards to FIG. 1, the microfluidic chip 202 may cause deformation of the cell 201 by introducing pressure waves into the cell probing chamber 211. More specifically, a pressure wave may be generated by a fluidic pump. In some examples, the fluidic pump includes a plurality of resistors such as actuators 217-1 and 217-2 fired at a frequency in the gigahertz range. The fluidic pump may include a thermal inkjet (TIJ) resistor (e.g., to generate a drive bubble), a piezo inkjet (PIJ) resistor, a magnetostrictive element, or another suitable pump (e.g., an integrated inertial pump). As the pressure wave applies pressure on the cell 201, the deformability of the cell 201 may be measured (e.g., responsive to the introduction of the pressure waves). To view the cell 201 and measure the deformability, the microfluidic chip 202 may include integrated optics and/or an external imaging system. The integrated optics may include lenses, such as micro-lenses packaged with the microfluidic chip, or flat-lenses which are fabricated directly or packaged with the microfluidic capping layer, or imaged through lens-less computational microscopy.

Although FIG. 2 illustrates a cross-shaped microfluidic device, examples are not so limited. For instance, in various examples, the apparatus includes a fluidic channel, with fluidic pumps disposed on opposing ends to control the flow of a biologic sample therethrough. As an illustration, the fluidic channel may be a channel with an input and an output on a side opposing the input. The biologic sample may flow along an axis from the input to the output. An actuator, or a plurality of actuators may be disposed within the fluidic channel. For instance, an actuator may be disposed within the fluidic channel and arranged to generate a pressure wave traversing the axis of the fluid flow. Additionally and/or alternatively, a plurality of actuators may be disposed within the fluidic channel and arranged to generate the pressure wave traversing the axis of the fluid flow.

Figure 3:
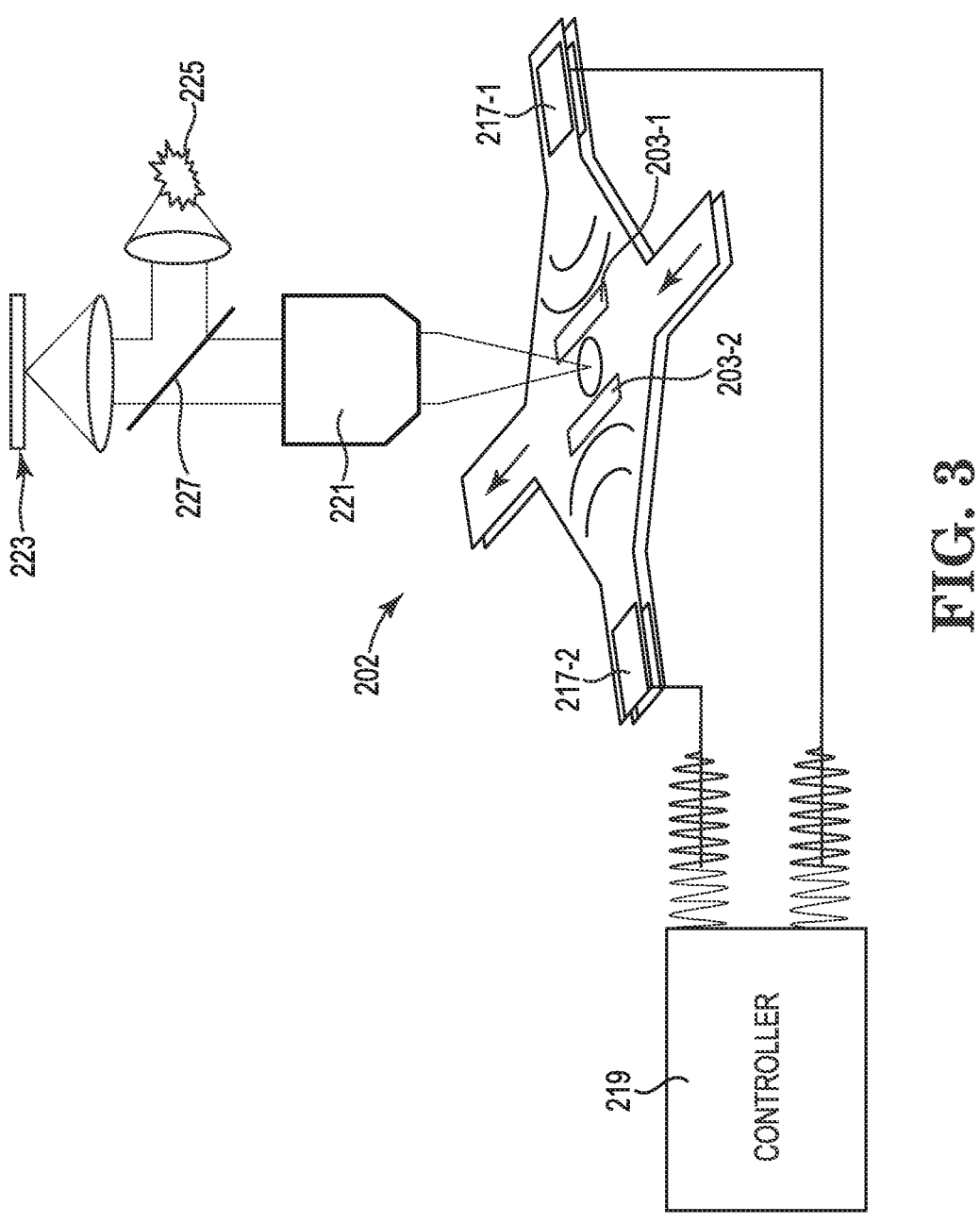
FIG. 3 further illustrates an example apparatus for measuring deformability of a cell responsive to a pressure wave, consistent with the present disclosure.

FIG. 3 further illustrates an example apparatus 202 for measuring deformability of a cell responsive to a pressure wave, consistent with the present disclosure. More particularly, FIG. 3 illustrates the apparatus 202 with a coupled controller 219, and an imaging array. As illustrated, the controller 219 may be coupled to the fluidic pump. In the example illustrated in FIG. 3, the fluidic pump includes actuators 217-2 and 217-1. Examples are not so limited, and the fluidic pump may include a pump or a plurality of pumps disposed outside of apparatus 202. The controller 219 may coordinate the firing of the actuators 217-2 and 217-1 so as to create a pressure wave in the chamber 211. The controller 219 may be communicatively coupled to the actuators 217-2 and 217-1 to control a frequency of the pressure waves applied to the cell (e.g., 201 illustrated in FIG. 2).

In various examples, the controller 219 may include a non-transitory computer-readable medium storing executable instructions. For instance, the controller 219 may include instructions which, when executed by a processor, actuate the fluidic pump to generate a pressure wave within the cell probing chamber 211, and determine a deformability of the cell responsive to the pressure wave. As such, the controller 219 may include, or be coupled to, a processor capable of executing such instructions. Non-limiting examples of a controller include a central processing unit (CPU), a semiconductor-based microprocessor, a graphics processing unit (GPU), a microcontroller, special purpose logic hardware controlled by microcode or other hardware devices suitable for retrieval and execution of instructions stored in a non-transitory computer-readable storage medium. As such, controller 219 may include a non-transitory computer-readable storage medium (not independently illustrated in FIG. 3). The non-transitory computer-readable storage medium may be an electronic, magnetic, optical, or other physical storage device that contains or stores executable instructions. Thus, non-transitory computer-readable storage medium of controller 219 may be, for example, Random Access Memory (RAM), an Electrically Erasable Programmable Read-Only Memory (EEPROM), a storage device, an optical disc, etc.

In some examples, the fluidic pump includes a plurality of resistors 217-2, 217-1, and the controller 219 includes instructions to actuate the plurality of resistors 217-2, 217-1 in a step-wise manner to provide increasing pressure on the cell, and coordinate image capture of the cell with the actuation of the plurality of resistors 217-2, 217-1. For instance, the controller 219 may include instructions to actuate the resistors 217-2 and 217-1 at a specified frequency and with a specified amount of pressure. Each time the resistors 217-2 and 217-1 are actuated, the imaging array may capture an image of the cell within the cell probing chamber 211. The controller 219 may operate by capturing an image of the cell in the cell probing chamber 211 and applying the pressure wave. A delay increment defines the amount of time that elapses between application of the pressure wave and image capture using the imaging array. A non-limiting example delay is 1 microsecond ($\mu s$). Additionally and/or alternatively, the controller 219 may operate by capturing an image of the cell before, during, and after applying the pressure wave. As such, the image acquisition starts a fixed amount of time before the cell is deformed. By capturing the image of the cell before, during, and after applying the pressure wave, the non-deformed geometry is captured, as well as the early stages of the deformation.

In some examples, the controller 219 includes instructions to determine the deformability of the cell based on an amount of pressure to deform the cell and return to a base state, as captured by an imaging array communicatively coupled to the controller 219. For instance, a size, shape, and/or diameter of a cell may be measured before application of the pressure wave, and a size, shape, and/or diameter of the cell may be measured during application of the pressure wave. The amount of change in the size and/or diameter of the cell responsive to the pressure wave may be used to determine the deformability of the cell.

As illustrated in FIG. 3, the apparatus 202 may include an imagining array. For instance, the imaging array may include an image sensor 223, which may be a charge-couple device (CCD), a complementary metal-oxide-semiconductor (CMOS) imaging device, or any other suitable imaging sensor. The imaging array may further include a light source 225, a dichroic mirror 227, and an objective 221 to visualize the cell 201.

Figures 4A, 4B, 4C:
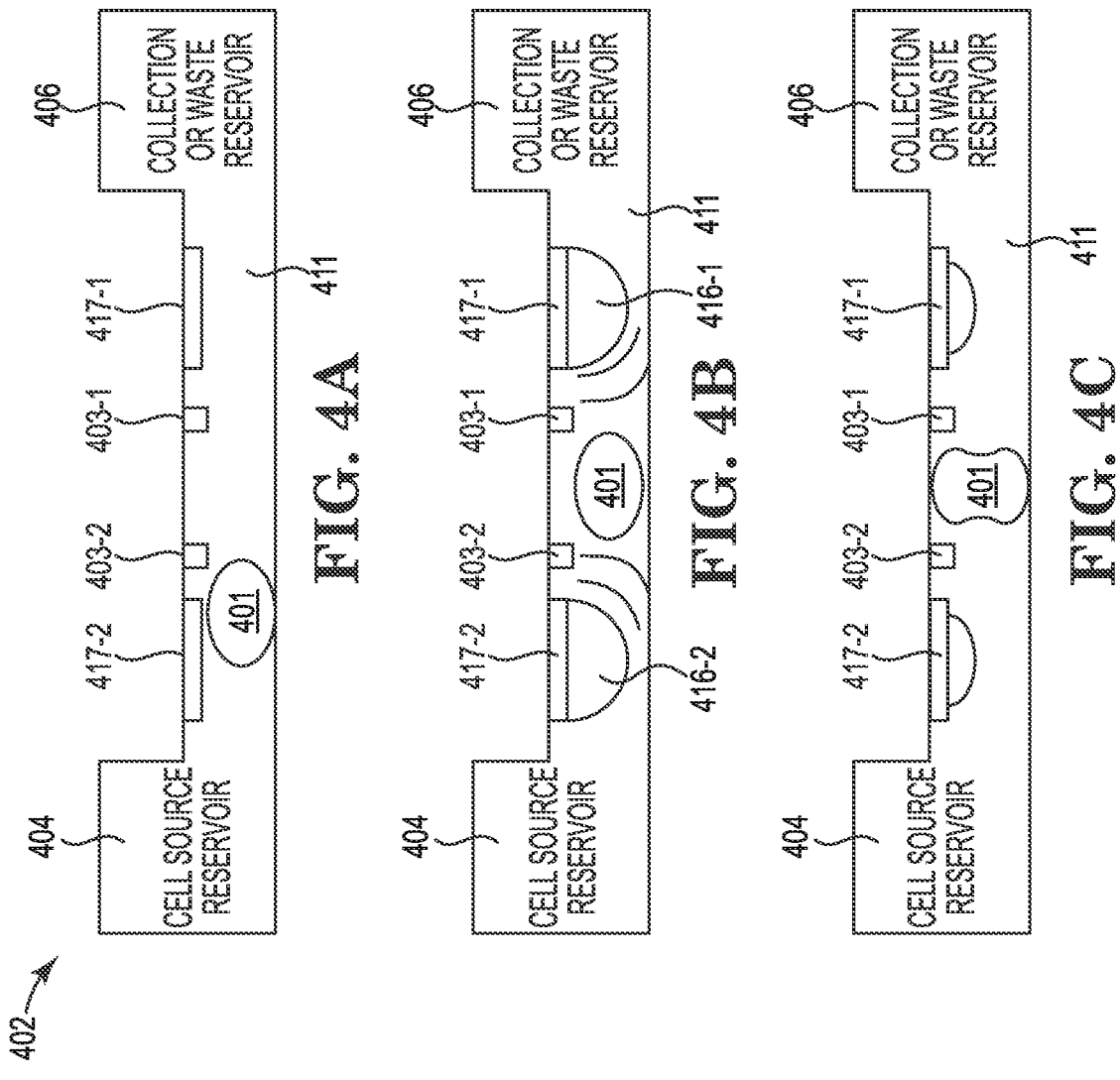
FIGS. 4A, 4B, and 4C further illustrate a side profile of a portion of an example apparatus for measuring deformability of a cell responsive to a pressure wave, consistent with the present disclosure.

FIGS. 4A, 4B, and 4C further illustrate a side profile of a portion of an example apparatus 402 for measuring deform- ability of a cell responsive to a pressure wave, consistent with the present disclosure. More particularly, FIG. 4A illustrates the apparatus 402 as a cell is moving into the apparatus 402, FIG. 4B illustrates the apparatus 402 while the cell is isolated within the cell probing chamber, and FIG. 4C illustrates the apparatus 402 as the cell is deformed.

As illustrated in FIG. 4A, the apparatus 402 includes a cell source reservoir 404, and a cell probing chamber 411 fluidically coupled to the cell source reservoir 404. The cell source reservoir 404 refers to or includes a fluidic channel or storage of a sample including cells. The cell probing cham- ber 411 includes a fluidic pump, such as resistors 417-2 and 417-1, to move a single cell 401 of a sample from the cell source reservoir 404 to the cell probing chamber 411. The cell probing chamber 411 also includes a sensor communi- catively coupled to the fluidic pump, the sensor to detect a position of the cell within the cell probing chamber. In the example illustrated in FIGS. 4A, 4B, and 4C, the sensor is illustrated as sensors 403-2 and 403-1. Example sensors may include an impedance sensor, a capacitance sensor, among other example sensors. On an opposing end of the apparatus 402, a collection or waste reservoir 406 may collect fluid samples after deformation analysis (e.g., rheologic pheno- typing). Additionally and/or alternatively, the cell probing chamber 411 may be fluidically coupled to additional fluidic channels for subsequent analysis. As illustrated, the cell source reservoir 404 may be disposed on a first end of the apparatus, and the apparatus 402 further includes a collec- tion reservoir 406 disposed on a second end of the apparatus opposite of the first end. In such examples, the fluidic pump includes a first resistor 417-2 proximate the first end (e.g., by cell source reservoir 404) and a second resistor 417-1 proximate the second end (e.g., by collection reservoir 406).

In the example illustrated in FIG. 4A, an integrated inertial pump 417-2 draws the cell 401 into the region between the two resistors 417-2 and 417-1. Impedance sensors 403-2 and 403-1 determine that the cell is in the correct position, and via feedback control (such as using controller 219 illustrated in FIG. 3) actuates the pull and push pumps 417-2 and 417-1 to position the cell 401.

As illustrated in FIG. 4B, the two resistors 417-2 and 417-1 opposite of the cell fire, deforming the cell 401. Pressure waves are generated by expanding steam bubbles 416-2 and 416-1, which are generated by resistors 417-2 and 417-1, respectively, firing. As illustrated in FIG. 4C, the cell is transiently deformed by the pulse, and its deformation and relaxation to a base state is observed by the imaging array illustrated in FIG. 3. The cell 401 may be interrogated by the pressure wave multiple times, including by different delays between the pressure pulse and the acquisition time of the image, and/or including by different effective frequencies that are present in differently sloped step functions as given rise by slower or faster expanding steam bubbles, controlled via power applied to the resistors 417-2 and 417-1 using controller 219 illustrated in FIG. 3. The cell may flow through the channel into the collection or waste reservoir 406, as discussed further herein.

Figures 5A, 5B, 5C:
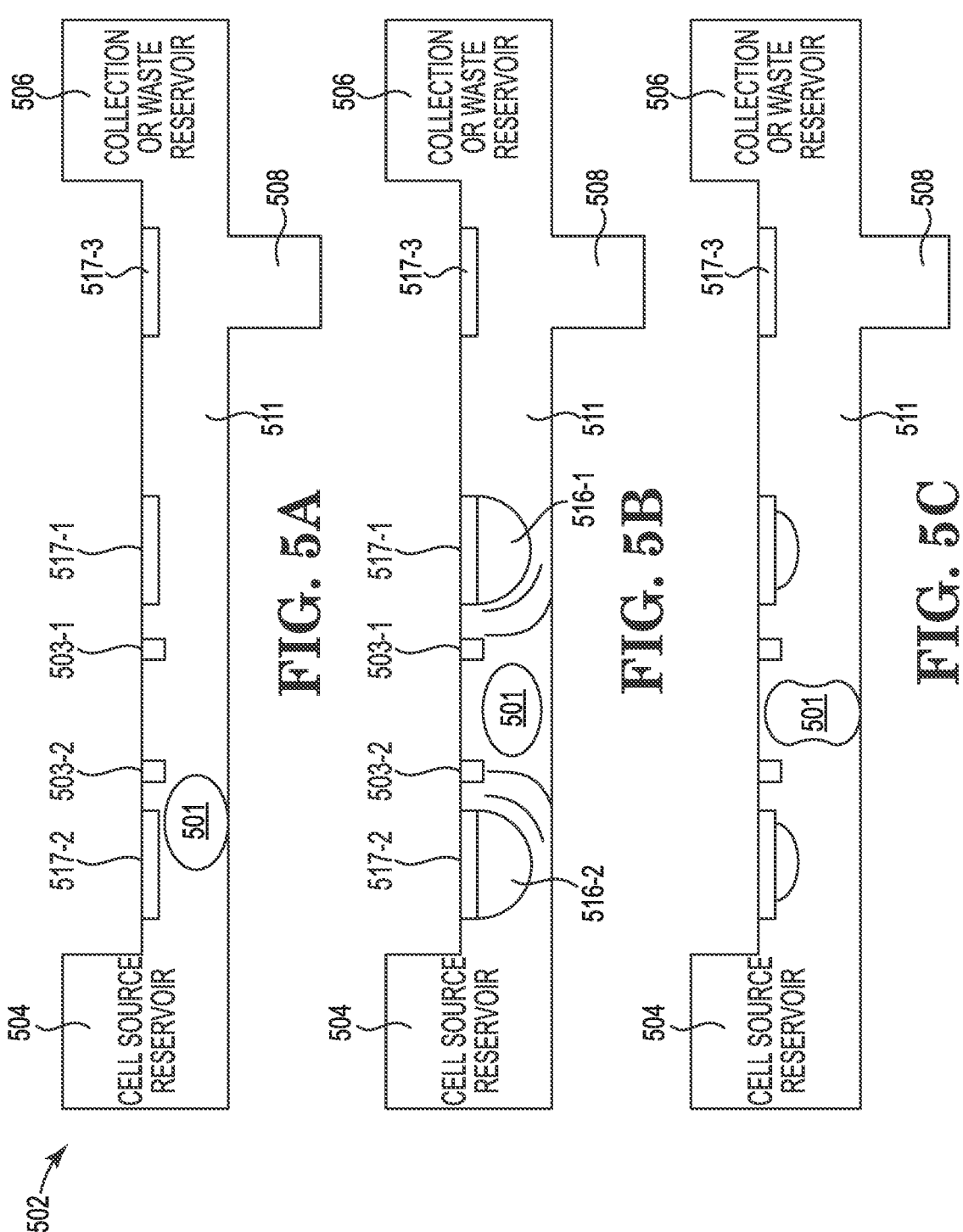
FIGS. 5A, 5B, and 5C further illustrate a side profile of a portion of an example apparatuses for measuring deformability of a cell responsive to a pressure wave, consistent with the present disclosure.

FIGS. 5A, 5B, and 5C further illustrate a side profile of a portion of an example apparatus 502 for measuring deform- ability of a cell responsive to a pressure wave, consistent with the present disclosure. Similar to the examples illus- trated in FIGS. 4A, 4B, and 4C, FIG. 5A illustrates the apparatus 502 as a cell is moving into the apparatus 502, FIG. 5B illustrates the apparatus 502 while the cell is isolated within the cell probing chamber, and FIG. 5C illustrates the apparatus 502 as the cell is deformed.

In the example illustrated in FIG. 5A, an integrated inertial pump 517-2 draws the cell 501 into the region between the two resistors 517-2 and 517-1. Sensors 503-2 and 503-1 determine that the cell is in the correct position, and via feedback control (such as using controller 219 illustrated in FIG. 3) actuates the pull and push pumps 517-2 and 517-1 to position the cell 501.

As illustrated in FIG. 5B, the two resistors 517-2 and 517-1 opposite of the cell fire, deforming the cell 501. Pressure waves are generated by expanding steam bubbles 516-2 and 516-1, which are generated by resistors 517-2 and 517-1, respectively, firing. As illustrated in FIG. 5C, the cell is transiently deformed by the pulse, and its deformation and relaxation to a base state is observed by the imaging array illustrated in FIG. 3. The cell may flow through the channel 511 into the collection or waste reservoir 506.

Additionally and/or alternatively, the cell 501 may be ejected out of the apparatus 502, such as for additional testing. Accordingly, the apparatus 502 further includes a resistor 517-3 for ejecting the cell out of a nozzle 508. As such, the cell may flow out of nozzle 508 or into the collection or waste reservoir 506 based on actuation of the resistor 517-3.

Figure 6:
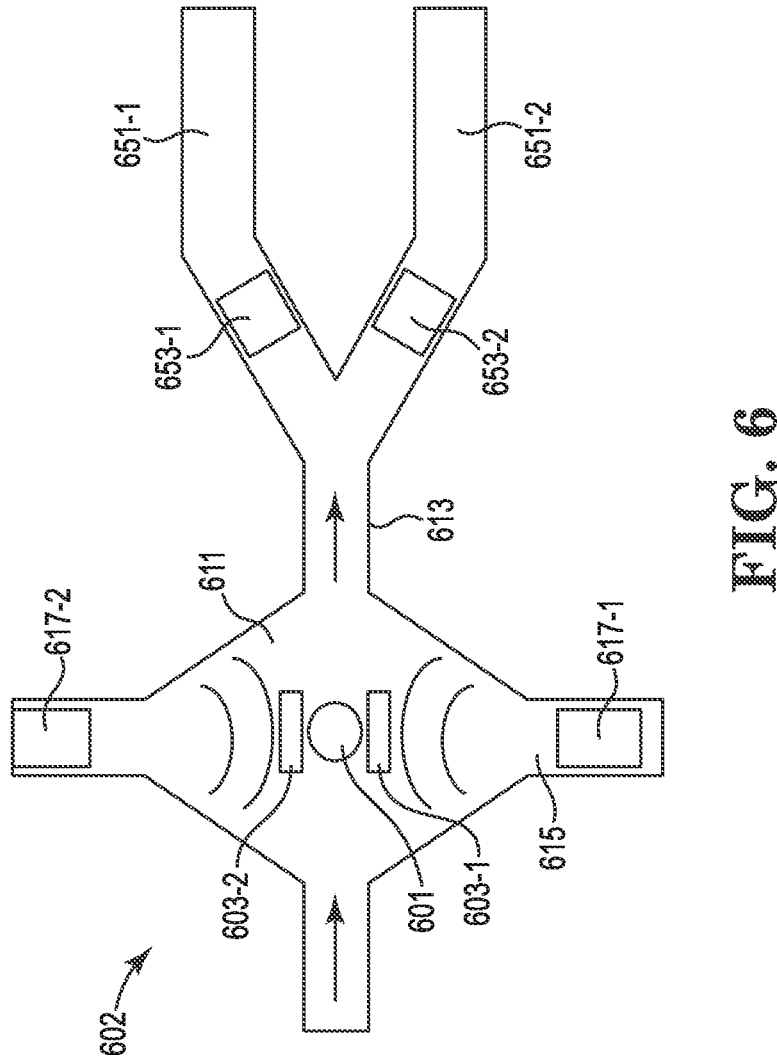
FIG. 6 further illustrates an example apparatus for measuring deformability of a cell responsive to a pressure wave, consistent with examples of the present disclosure.

FIG. 6 further illustrates an example apparatus 602 for measuring deformability of a cell responsive to a pressure wave, consistent with examples of the present disclosure. As illustrated in FIG. 6, a plurality of channels 651-1 and 651-2 may be fluidically coupled to the cell probing chamber 611 to sort and concentrate cells after deformation testing. For instance, as the properties of the cell 601 are determined, one of a plurality of pumps 653-1 and 653-1 may fire to pull the cell 601 into the associated channel, 651-1 or 651-2, respec- tively. As an example, if a deformability of the cell 601 is detected to be above a particular threshold, then the cell 601 may be drawn into channel 651-1 by firing pump 653-2 to push the cell 601 into channel 651-1. Similarly, if a deform- ability of the cell 601 is detected to be below a particular threshold, then the cell 601 may be drawn into channel 651-2 by firing pump 653-1 to push the cell 601 into channel 651-2. Additionally and/or alternatively, piezoelectric ele- ments 617-1 and 617-2 may fire to push the cell 601 into channel 651-2 or channel 651-1. Although FIG. 6 illustrates two fluidic channels fluidically coupled to the cell probing chamber 611, examples are not so limited, and any number of fluidic channels may be coupled to the cell probing chamber 611. Multiple channels may be of particular interest for cell sorting and concentration in different cell collectors.

As discussed with regards to FIG. 2 and FIG. 3, a sensor may be disposed within the cell probing chamber 611 to determine the location of the cell 601, and may be used to coordinate firing of elements 617-1 and 617-2 and image capture while the cell is within the cell probing chamber. A non-limiting example of a sensor is illustrated in FIG. 6 as sensors 603-2 and 603-1.

Figure 7:
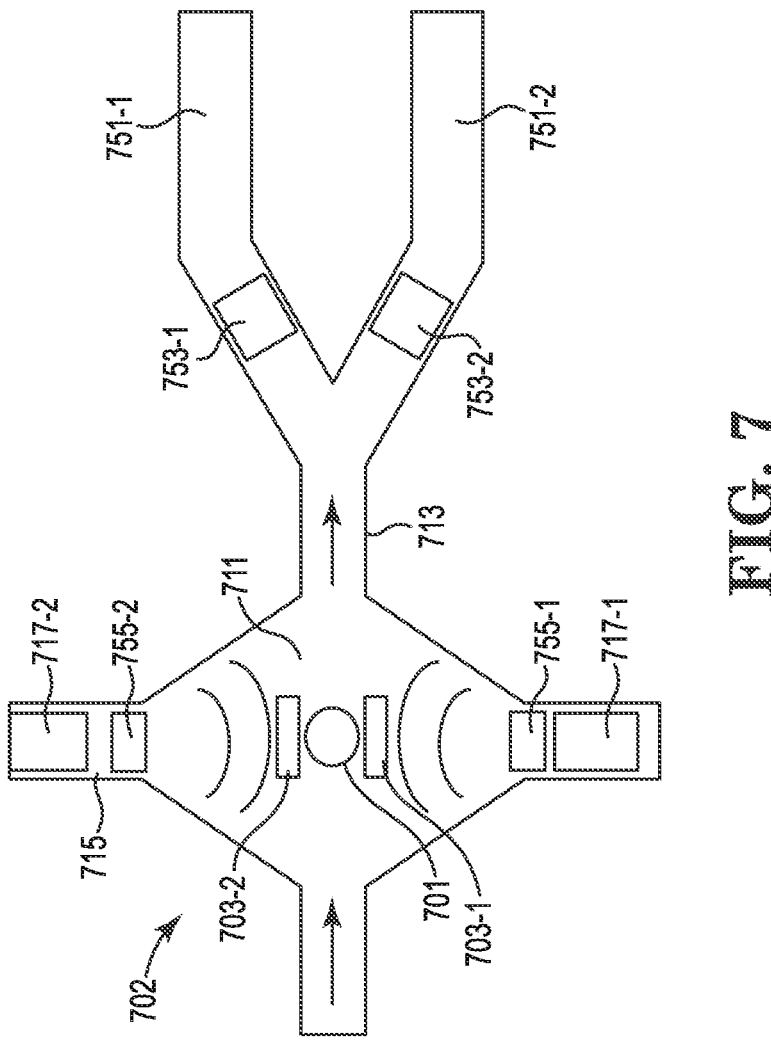
FIG. 7 further illustrates an example apparatus for measuring deformability of a cell responsive to a pressure wave, consistent with examples of the present disclosure.

FIG. 7 further illustrates an example apparatus 702 for measuring deformability of a cell responsive to a pressure wave, consistent with examples of the present disclosure. Similar to FIG. 6, the apparatus 702 includes a plurality of channels 751-1 and 751-2 may be fluidically coupled to the cell probing chamber 711 to sort cells after deformation testing. For instance, as the properties of the cell 701 are determined, one of a plurality of pumps 753-1 and 753-2 may fire to pull the cell 701 into the associated channel, 751-1 or 751-2, respectively. Additionally and/or alternatively, piezoelectric elements 717-1 and 717-2 may fire to push the cell 701 into channels 751-1 or 751-2. Moreover, resistors 755-1 and 755-2 may be disposed adjacent to piezoelectric elements 717-1 and 717-2. The resistors 755-1 and 755-2 may also be fired to direct the flow of the cell 701 into one of channels 751-1 or 751-2. Although FIG. 7 illustrates two fluidic channels fluidically coupled to the cell probing chamber 711, examples are not so limited, and any number of fluidic channels may be coupled to the cell probing chamber 711.

As discussed with regards to FIG. 2 and FIG. 3, a sensor may be disposed within the cell probing chamber 711 to determine the location of the cell 701, and may be used to coordinate firing of elements 717-1 and 717-2 and image capture while the cell is within the cell probing chamber. A non-limiting example of a sensor is illustrated in FIG. 7 as sensors 703-2 and 703-1.

Figure 8:
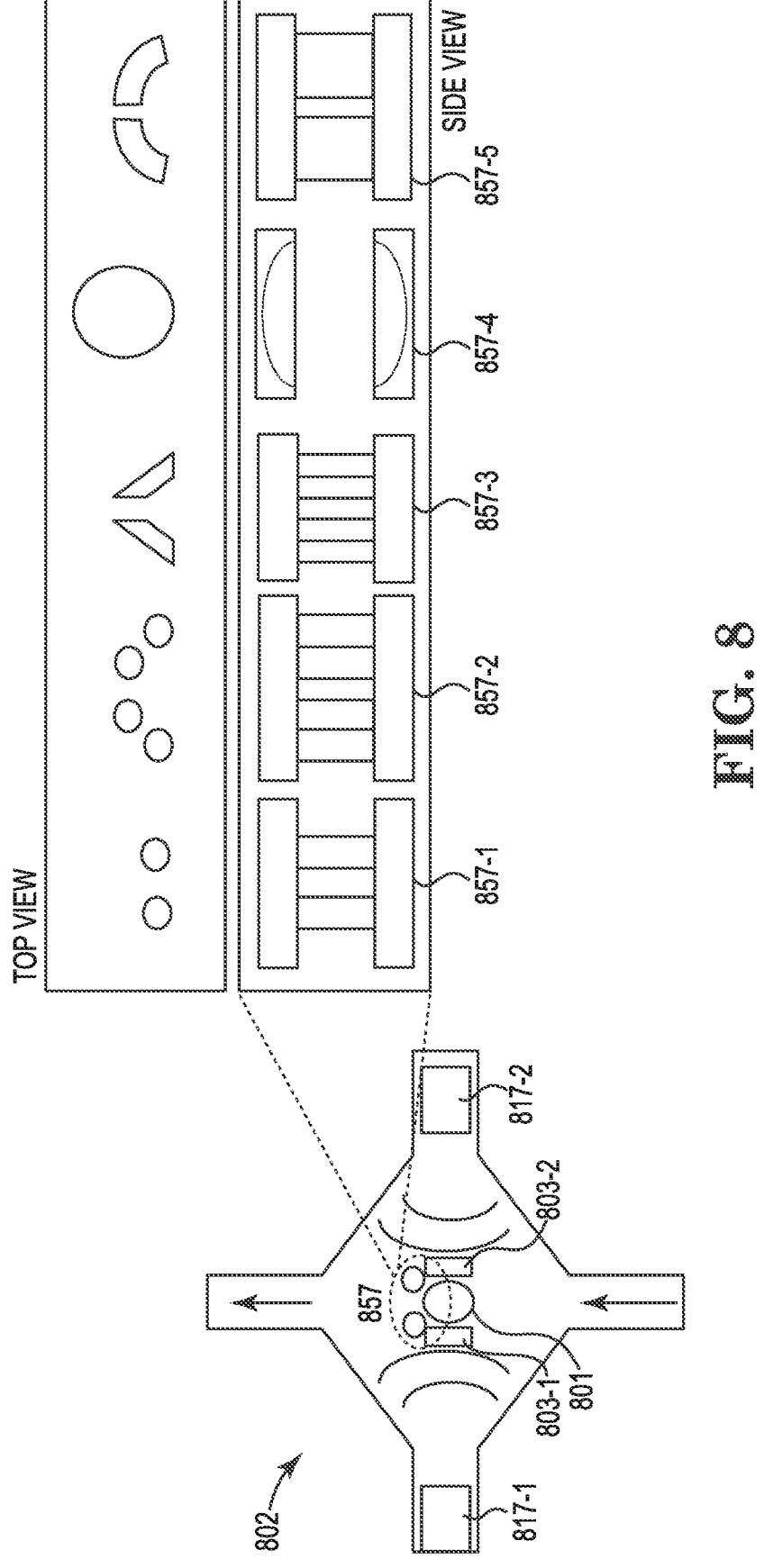
FIG. 8 illustrates an example apparatus for measuring deformability of a cell including barriers to contain a cell, consistent with examples of the present disclosure.

FIG. 8 illustrates an example apparatus 802 for measuring deformability of a cell including barriers to contain a cell, consistent with examples of the present disclosure. For instance, in various examples, apparatus 802 may include a barrier 857 to contain the cell 801. Examples 857-1, 857-2, 857-3, 857-4 and 857-5 illustrate various designs of a barrier 857 that may be used. As illustrated, barrier 857-1 may include two pillars disposed orthogonal to the flow of the biologic sample to trap the cell 801 for measuring deformability. Once measurements are obtained, elements 817-1 and/or 817-2 may actuate to move the cell 801 around the barrier 857-1.

As a further example, a pillar trap 857-2 may be disposed orthogonal to the flow of the biologic sample. Similar to the two pillars illustrated in 857-1, the pillar trap 857-2 may include a plurality of vertically aligned pillars to trap the cell 801 for measuring deformability. Once measurements are obtained, piezoelectric elements 817-1 and/or 817-2 may actuate to move the cell 801 around the barrier 857-2.

In yet another example, a funnel 857-3 may be disposed orthogonal to the flow of the biologic sample. The funnel 857-3 may include two tapered members, vertically aligned orthogonal to the flow of the biologic sample. The tapered members may trap the cell 801 for measuring deformability. Once measurements are obtained, piezoelectric elements 817-1 and/or 817-2 may actuate to move the cell 801 around the barrier 857-3.

Furthermore, a depression 857-4 may be disposed orthogonal to the flow of the biologic sample. The depression 857-4 may include a recessed portion of the substrate and lid of the microfluidic device 802. The depression 857-4 may trap the cell 801 for measuring deformability. Once measurements are obtained, piezoelectric elements 817-1 and/or 817-2 may actuate to move the cell 801 out of the depression 857-4.

Yet further, a wall 857-5 may be disposed orthogonal to the flow of the biologic sample. The wall 857-5 may include a plurality of curved orthogonal pillars within the microfluidic device 802. The wall 857-5 may be disposed orthogonal to the flow of the biologic sample and may trap the cell 801 for measuring deformability. Once measurements are obtained, piezoelectric elements 817-1 and/or 817-2 may actuate to move the cell 801 out of the depression 857-5.

Although 857-1, 857-2, 857-3, 857-4, and 857-5 illustrate different kinds of structures that can facilitate the trapping of the cell 801 in the cell probing chamber, different and/or additional barriers 857 may be used. In any scenario, the cell 801 may be released from the barrier 857 by reversing the flow momentarily and providing a lateral flow simultaneously by actuating the piezoelectric elements 817-1 and/or 817-2 in an asymmetric way, before re-establishing the flow in the direction illustrated.

As discussed with regards to FIG. 2 and FIG. 3, a sensor may be disposed within the cell probing chamber to determine the location of the cell 801, and may be used to coordinate firing of elements 817-1 and 817-2 and image capture while the cell is within the cell probing chamber. A non-limiting example of a sensor is illustrated in FIG. 8 as sensors 803-2 and 803-1.

Figures 9A, 9B:
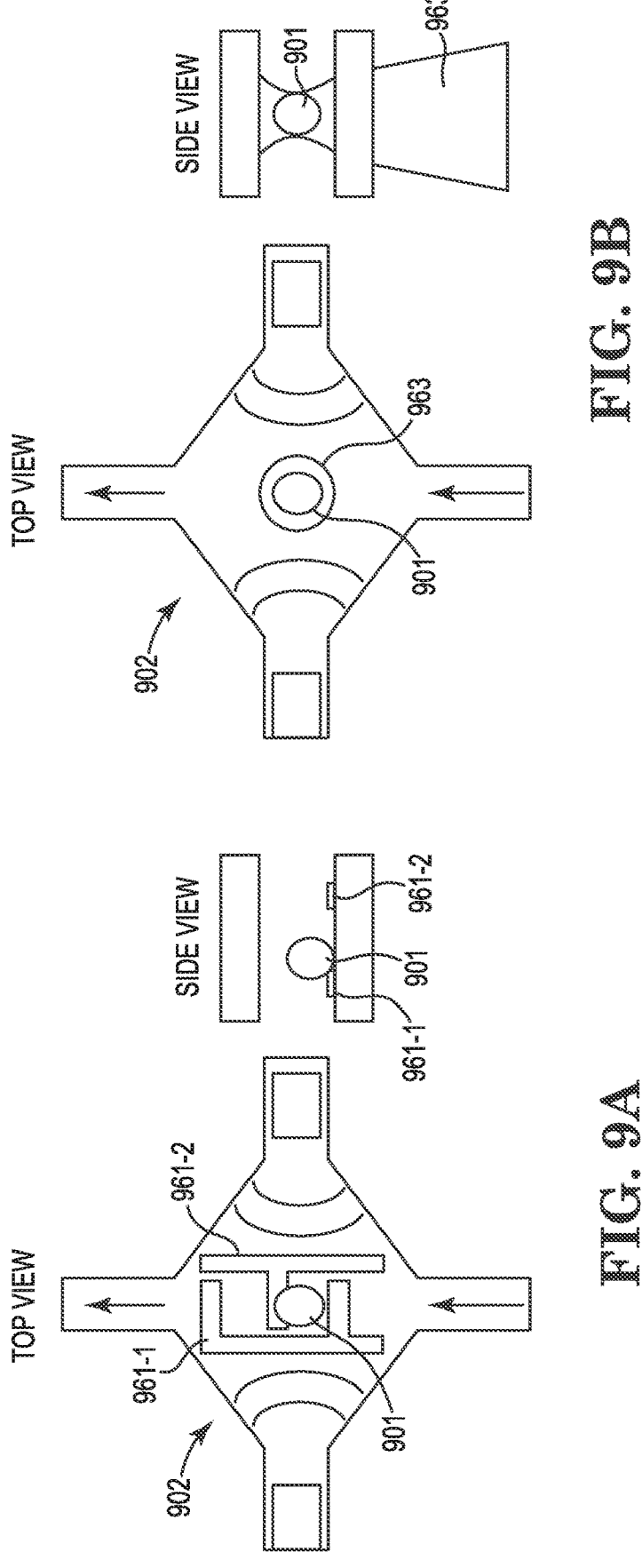
FIGS. 9A and 9B illustrate example apparatuses for measuring deformability of a cell including non-mechanical mechanisms to contain a cell, consistent with examples of the present disclosure.

FIGS. 9A and 9B illustrate example apparatuses 902 for measuring deformability of a cell including non-mechanical mechanisms to contain a cell 901, consistent with examples of the present disclosure. More particularly, FIG. 9A illustrates an example apparatus 902 for measuring deformability of a cell including three-dimensional electrodes 961-1 and 961-2, consistent with the present disclosure. Using a dielectrophoresis (DEP)-based cell-separation method, three-dimensional electrodes 961-1 and 961-2 may be disposed on the substrate of the microfluidic chip 902 and may hold the cell 901 at a point of high electric field gradient. Accordingly, in some examples, the apparatus 902 may include a plurality of electrodes 961-1 and 961-2 disposed in a substrate of the cell probing chamber, the plurality of electrodes 961-1 and 961-2 to hold the cell 901 in the cell probing chamber by dielectrophoresis.

Similarly, FIG. 9B illustrates an example apparatus 902 for measuring deformability of a cell including a laser beam gradient 963, consistent with the present disclosure. In such examples, the laser beam gradient 963 may be created by a laser optical system. The laser beam gradient 963 forms a single-beam gradient force trap to hold the cell 901 in the cell probing chamber. The cell 901 may be released from the cell probing chamber by terminating the electric field in FIG. 9A, or by terminating the laser beam gradient in FIG. 9B. As discussed herein, while secured as illustrated in FIG. 9A and/or 9B, rheologic phenotyping may be performed on cell 901.

Figure 10:
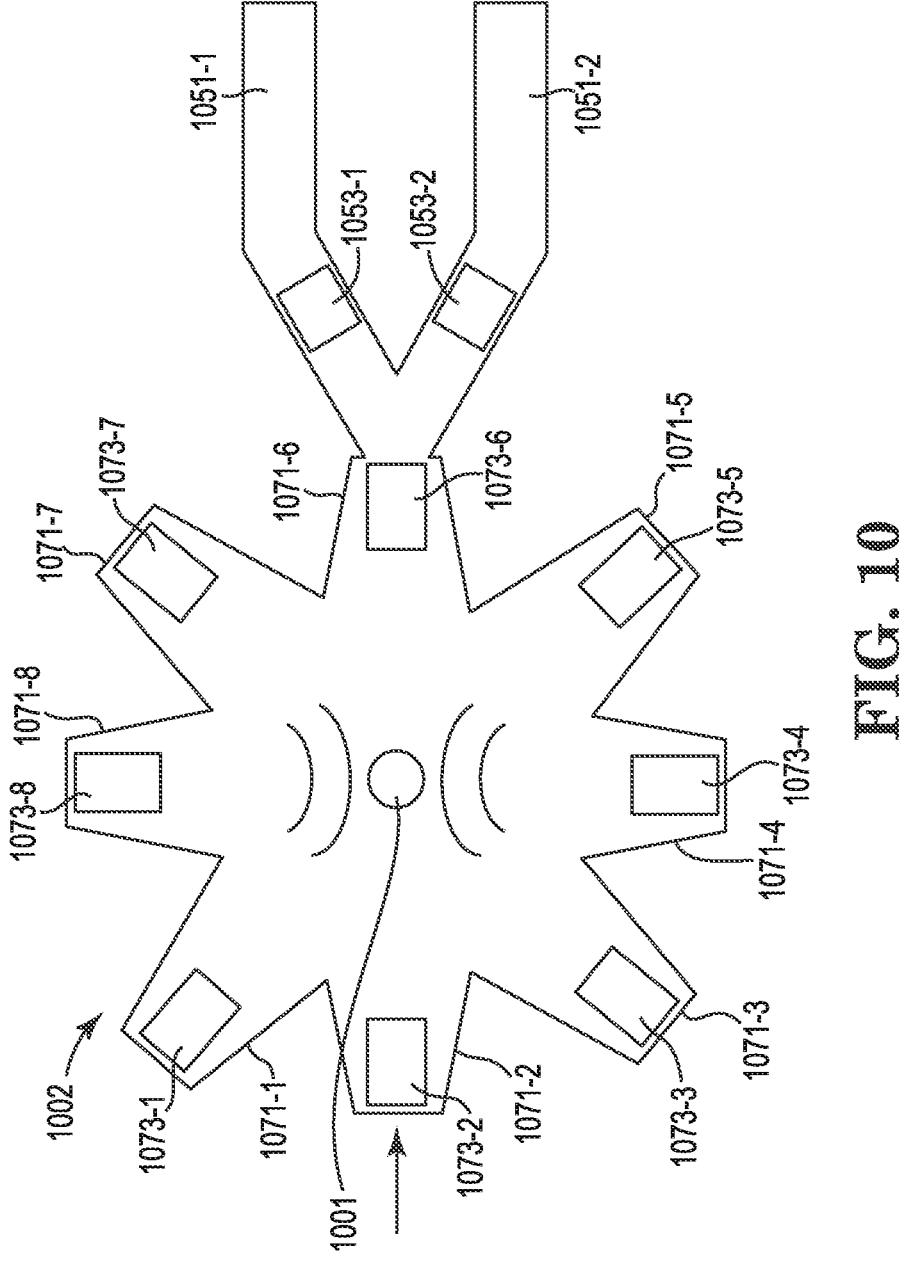
FIG. 10 illustrates an example apparatus for measuring deformability of a cell responsive to a pressure wave, consistent with the present disclosure.

FIG. 10 illustrates an example apparatus 1002 for measuring deformability of a cell responsive to a pressure wave, consistent with the present disclosure. As illustrated in FIG. 10, a plurality of diagonal channels 1071-1, 1071-2, 1071-3, 1071-4, 1071-5, 1071-6, 1071-7, and 1071-8 (referred to collectively as diagonal channels 1071) may be fluidically coupled to the cell probing chamber. Each diagonal channel 1071 may further include a piezoelectric element 1073-1, 1073-2, 1073-3, 1073-4, 1073-5, 1073-6, 1073-7, and 1073-8 (referred to collectively as piezoelectric elements 1073). The piezoelectric elements 1073 may provide a variety of combinations for generating a pressure wave, and/or provide a variety of combinations for moving the cell 1001 through the apparatus 1002. For instance, a subset of the piezoelectric elements 1073 may be selected for firing to create the pressure wave. Additionally and/or alternatively, a subset of the piezoelectric elements 1073 may be selected for moving the cell 1001 into channels 1051-1 or 1051-2. Moreover, pumps 1053-1 and/or 1053-2 may assist in directing the flow of the cell 1001 into a respective channel. As discussed herein, rheologic phenotyping may be performed on cell 1001, and the various piezoelectric elements 1073 may separately actuate to direct the cell 1001 to different locations in the device 1002.

FIG. 11 illustrates an example apparatus 1102 for measuring deformability of a cell responsive to a pressure wave, consistent with the present disclosure. Particularly, FIG. 11 illustrates an apparatus 1102 including an integrated optics system. As illustrated in FIG. 11, the apparatus 1102 may include a lateral fluidic channel 1115, a longitudinal fluidic channel 1113, and a cell probing chamber 1111. The cell probing chamber 1111 may include a transparent lid 1175 disposed over a base substrate 1177 to form a channel 1179 therethrough. An integrated lens 1181 may be disposed on the transparent lid 1175 of the cell probing chamber 1111. The integrated lens 1181 may focus light from the cell 1101 in the cell probing chamber 1111 to a sensor array 1183.

The integrated lens 1181 may comprise a plurality of materials. For instance, the integrated lens 1181 may comprise a zone plate, a Fresnel lens, metasurfaces, or other suitable lenses and/or micro-lenses for a variety of imaging modalities and optical configurations (e.g., infinity corrected, point-to-point magnification, integrated source, fluorescence, etc.). If a flat lens is used, the sensor may be in close proximity to the channel and substrate to create a compact package. As discussed with regards to FIG. 2, the integrated lens may be used to capture images of cells 1101 in the cell probing chamber 1111 during rheologic phenotyping.

FIGS. 12A, 12B, 12C, and 12D further illustrate side views of an apparatus 1202 for measuring deformability of a cell responsive to a pressure wave, consistent with the present disclosure. Particularly, FIGS. 12A, 12B, 12C, and 12D illustrate an apparatus 1202 with parallel cell probing chambers for multiplexed analysis. As illustrated, a plurality of cell probing chambers 1235-1, 1235-2, 1235-3 may be fluidically coupled to the cell source reservoir 1204. In such examples, each cell probing chamber includes a fluidic pump to move a single cell of a sample from the cell source reservoir 1204 to the respective cell probing chamber. Each cell probing chamber includes a plurality of resistors disposed between the cell source reservoir and the fluidic pump. For instance, referring to cell probing chamber 1235-1, resistors 1230-1 and 1230-2 may be disposed within cell probing chamber 1235-1, as discussed herein. Additionally and/or alternatively, piezoelectric elements may be disposed within the cell probing chamber 1235-1 and may be used to deform the cell. Sensors 1231-1 and 1231-2 may also be disposed between resistors 1230-1 and 1230-2 as discussed herein. Similarly, cell probing chamber 1235-2 includes resistors 1230-3 and 1230-4, as well as sensors 1231-3 and 1231-4. Moreover, cell probing chamber 1235-3 includes resistors 1230-5 and 1230-6, as well as sensors 1231-5 and 1231-6. Each of the cell probing chambers may also include a respective nozzle to eject fluid, including a cell. Accordingly, each cell probing chamber may include a nozzle and a resistor to eject fluid therefrom.

Figures 12A, 12B, 12C, 12D:
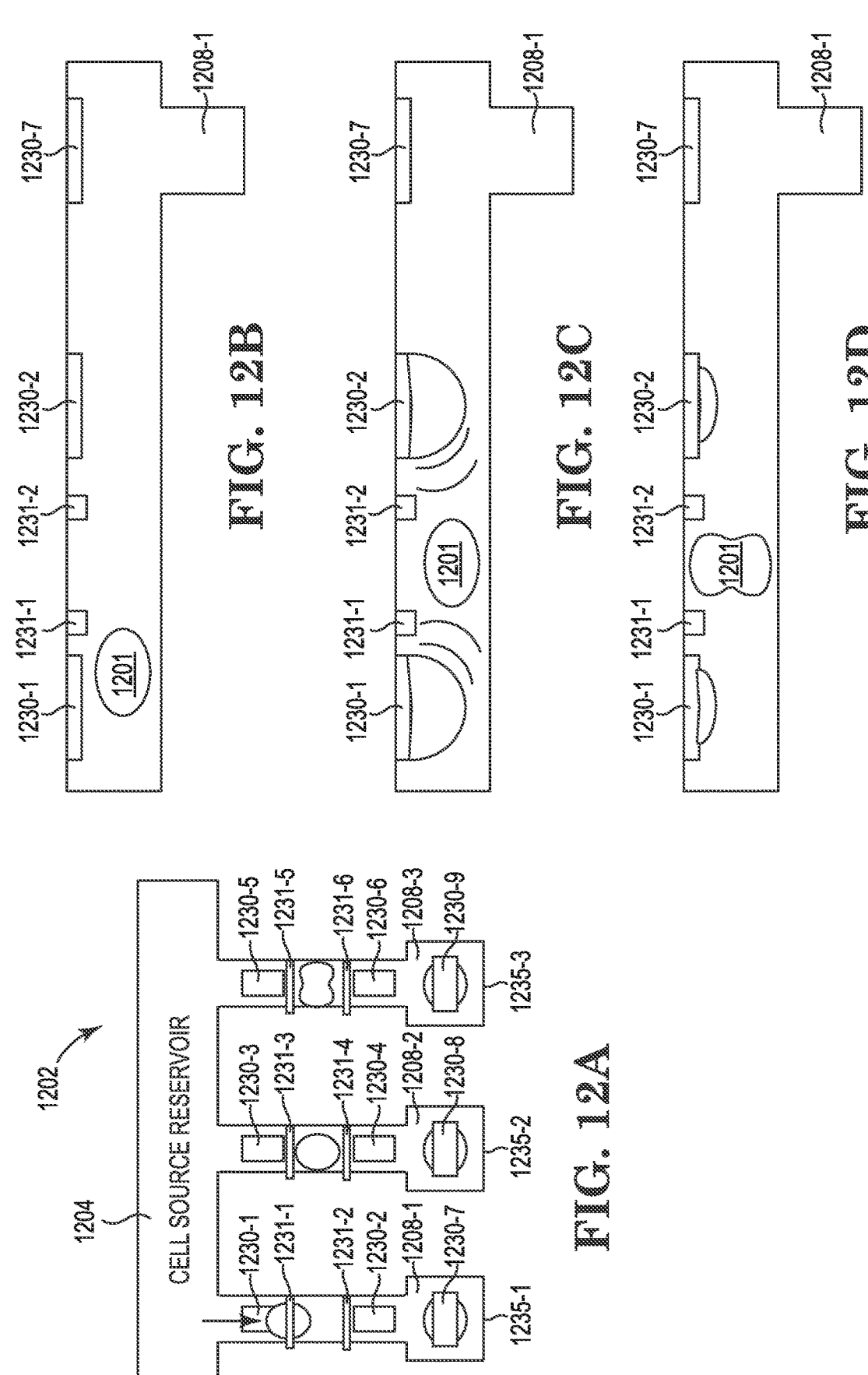
FIGS. 12A, 12B, 12C, and 12D further illustrate side views of an apparatus for measuring deformability of a cell responsive to a pressure wave, consistent with the present disclosure.

Referring to FIG. 12A, cell probing chamber 1235-1 includes nozzle 1208-1 and resistor 1230-7, cell probing chamber 1235-2 includes nozzle 1208-2 and resistor 1230-8, cell probing chamber 1235-3 includes nozzle 1208-3 and resistor 1230-9.

In various examples, the controller (e.g., controller 219 illustrated in FIG. 3) may further include instructions to independently actuate the fluidic pump of a respective cell probing chamber to move a cell into the cell probing chamber, independently actuate the plurality of resistors to apply a pressure wave to the cell while the cell is isolated in the respective cell probing chamber, and determine a deformability of the cell in each respective cell probing chamber responsive to the respective pressure wave. While the controller is not illustrated in FIGS. 12A, 12B, 12C, and 12D for the ease of illustration, the controller may be coupled to each resistor and each sensor of apparatus 1202. As such, referring to FIGS. 12B, 12C, and 12D, each cell probing chamber 1235 may be independently operated to move a cell from the cell source reservoir 1204 to the respective nozzle. FIGS. 12B, 12C, and 12D illustrate side views of cell probing chamber 1235-1. In operation, pump 1230-7 draws a cell into region between the two resistors (e.g., 1230-1 and 1230-2). Sensors 1231-1 and 1231-2 determine that the cell is in the correct position, and via feedback control controls the pump 1230-7 to position the cell. The two resistors 1230-1 and 1230-2 opposite of the cell fire, deforming the cell. Meanwhile an imaging array observes the deformation. The cell may be interrogated by the pressure wave multiple times, including by different effective frequencies that are present in differently step-wise functions as given rise by slower or faster expanding steam bubbles, controlled via applied power to the resistor by the controller.

FIGS. 13A, 13B, 13C, 13D, 13E, and 13F illustrate a variety of different apparatuses for measuring deformability of a cell responsive to a pressure wave, consistent with the present disclosure. For instance, FIG. 13A illustrates an apparatus 1361 with a first arrangement of cell probing chambers, FIG. 13B illustrates an apparatus 1362 with a second arrangement of cell probing chambers, FIG. 13C illustrates an apparatus 1363 with a third arrangement of cell probing chambers, FIG. 13D illustrates an apparatus 1364 with a fourth arrangement of cell probing chambers, FIG. 13E illustrates an apparatus 1365 with a fifth arrangement of cell probing chambers, and FIG. 13F illustrates an apparatus 1366 with a sixth arrangement of cell probing chambers.

While each separate structural element in FIGS. 13A, 13B, 13C, 13D, 13E, and 13F are not numbered for the sake of readability, similar elements to those discussed with regards to FIGS. 12A, 12B, 12C, and 12D are illustrated. A plurality of fluidic channels are arranged in parallel, such that a plurality of cells may be interrogated at a same time. For instance, as illustrated in FIG. 13A (and discussed with regards to FIG. 12A), three cell probing chambers may be arranged in parallel, and each cell probing chamber has a nozzle to eject the cell into a particular location. Also as discussed with regards to FIGS. 12A, 12B, 12C, and 12D, each channel may include a plurality of resistors. Each channel may also include a plurality of sensors, and a same imaging array may be used to view the change of shape of the cells.

While FIG. 13A illustrates the resistors arranged serially in each respective cell probing chamber, examples are not so limited. As illustrated in FIG. 13B resistors 1367-1 and 1367-2 may be disposed orthogonally to the cell probing chamber, such that the pressure wave is applied to the cell in an orthogonal direction to the flow of fluid. While FIG. 13B illustrates two resistors, less or more resistors may be included. For instance, FIG. 13C illustrates a single resistor 1368 disposed orthogonally to the cell probing chamber. A solid wall of the cell probing chamber may reflect the pressure wave generated by the resistor 1368, thereby applying the pressure wave to a cell. FIG. 13D illustrates an additional arrangement in which two resistors 1369-2 and 1369-4 are disposed orthogonally to the cell probing chamber and two resistors 1369-1 and 1369-3 are disposed serially in the cell probing chamber. As discussed with regards to FIGS. 12A, 12B, 12C, and 12D, each of the plurality of resistors (e.g., 1369-1, 1369-2, 1369-3, 1369-4) may be individually actuated by a controller, such as controller 219 illustrated in FIG. 3. Additionally and/or alternatively, each of the plurality of resistors may be actuated in coordination with other ones of the plurality of resistors. Additionally, a plurality of sensors 1370-1, 1370-2, 1370-3, and 1370-4 may be arranged within the cell probing chamber to determine a position of a cell within the cell probing chamber. As with resistors 1369-1, 1369-2, 1369-3, and 1369-4, each of the plurality of sensors 1370-1, 1370-2, 1370-3, and 1370-4 may be communicatively coupled to the controller (e.g., controller 219 illustrated in FIG. 3) and used to control firing of resistors 1369-1, 1369-2, 1369-3, and 1369-4.

As illustrated in FIG. 13E, cells may be deposited into a waste chamber or cell receiving chamber 1371, rather than being ejected out of a nozzle as illustrated in FIGS. 13A, 13B, 13C, and 13D. FIG. 13F further illustrates an example apparatus 1366, in which a plurality of resistors are disposed in the cell probing chamber, similar to FIG. 13D. Similar to FIGS. 13D and 13E, two resistors may be disposed orthogonally in the cell probing chamber, and two resistors may be disposed serially in the cell probing chamber. Further, a nozzle 1372 may eject cells by firing resistor 1373, or cells may be deposited into the cell repository or waste chamber 1371.

FIGS. 14A, 14B, 14C, 14D, 14E, 14F, 14G, and 14H illustrate a variety of different apparatuses for measuring deformability of a cell responsive to a pressure wave, including recirculation loops, consistent with the present disclosure. For the ease of illustration, similar elements are not numbered in each of FIGS. 14A, 14B, 14C, 14D, 14E, 14F, 14G, and 14H.

Figures 14A, 14B, 14C, 14D:
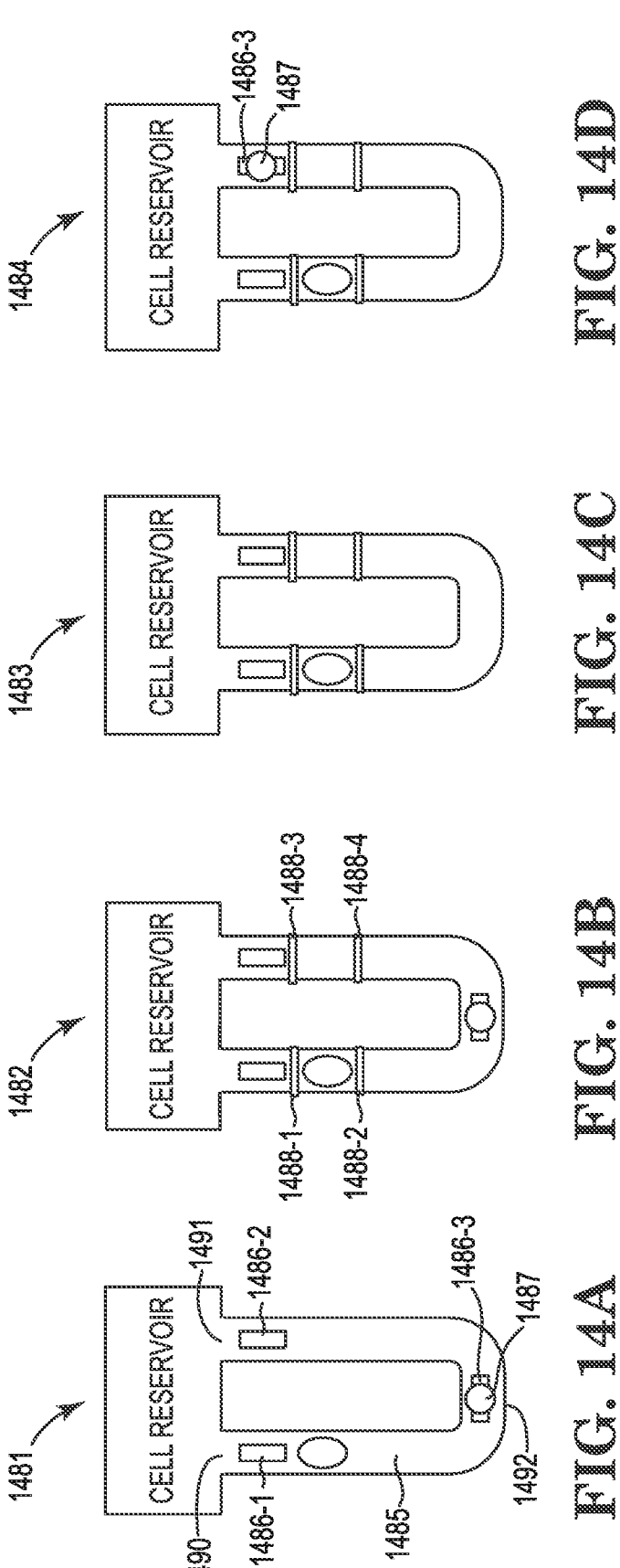
FIGS. 14A, 14B, 14C, 14D, 14E, 14F, 14G, and 14H illustrate a variety of different apparatuses for measuring deformability of a cell responsive to a pressure wave, including recirculation loops, consistent with the present disclosure.

FIG. 14A illustrates an apparatus 1481 including a recirculation loop 1485 including a first end 1490 coupled to a cell reservoir, a distal loop 1492, and a second end 1491 coupled to the cell reservoir. Additionally, an integrated inertial pump, either pump 1486-1 or pump 1486-2, may draw a cell from the cell reservoir into the region between resistor 1486-1 and resistor 1486-2. Resistor 1486-1 and/or resistor 1486-2 may actuate (responsive to a signal from controller 219 illustrated in FIG. 3), causing deformation of the cell. Meanwhile an imaging array (as discussed in regards to FIG. 3) observes the deformation. The resistors 1486-1 and 1486-2 may fire independently of one another to generate a flow within recirculation loop 1485. As such, the cell may move back into the cell reservoir or be ejected out of nozzle 1487 by actuating resistor 1486-3.

As illustrated in FIG. 14B, more or fewer components may be added to the apparatus. For instance apparatus 1482 includes all of the components of apparatus 1481, as well as sensors 1488-1, 1488-2, 1488-3, and 1488-4. The sensors may determine that the cell is in the correct position, and via a feedback control (e.g., via controller 219 illustrated in FIG. 3) actuate the resistors 1486-1, 1486-2 to position the cell. Apparatus 1483 illustrated in FIG. 14C includes all of the components of FIG. 14B, with the exception of resistor 1486-3 and nozzle 1487. As such, apparatus 1483 recirculates cells from the cell reservoir, through the recirculation loop 1485, and back into the cell reservoir. Apparatus 1484 illustrated in FIG. 14D includes the components of FIG. 14C, except resistor 1486-2 is replaced with a resistor 1486-3 and nozzle 1487 structure. That is, in FIG. 14D, a cell may be pulled from the cell reservoir by actuating resistor 1486-1, the cell may be positioned within the recirculation loop 1485 using sensors 1488-1, 1488-2, 1488-3, and 1488-4, and then the cell may either be ejected from nozzle 1487 by actuating resistor 1486-3, or may be returned to the cell reservoir.

Figures 14E, 14F, 14G, 14H:
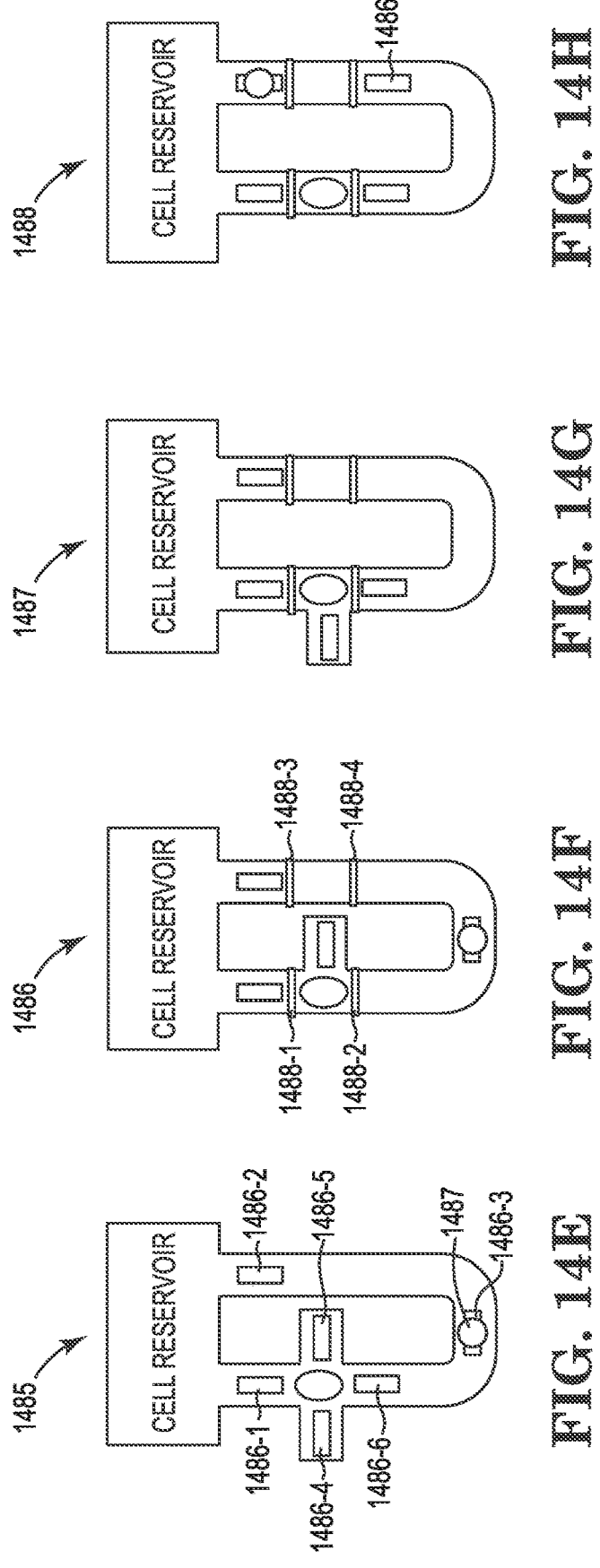

As illustrated in FIGS. 14E, 14F, 14G, and 14H, more or fewer components may be included. For instance, FIG. 14E illustrates an apparatus 1485 including additional resistors and without sensors. Similar to apparatus 1481, apparatus 1485 includes resistor 1486-1, and 1486-2, as well as resistor 1486-3 and nozzle 1487. In addition, apparatus 1485 includes an additional resistor 1486-6 disposed within the recirculation loop 1485. Moreover, apparatus 1485 includes resistors 1486-4 and 1486-5 disposed orthogonal to the recirculation loop 1485. As used herein, the recirculation loop refers to or includes a cell probing chamber shaped to circulate fluid out of and back into the cell reservoir, as illustrated. As such, in some examples, the cell probing chamber forms a recirculation loop 1485 fluidically coupled to the cell source reservoir at a first end 1490 of the recirculation loop 1485 and a second end 1491 of the recirculation loop 1485. As described herein, the fluidic pump (e.g., resistors 1486-1 and 1486-2) capable of moving cells within the cell probing chamber may be disposed proximal to the cell source reservoir at the first end 1490 of the recirculation loop 1485 and the resistor 1486-2 is disposed proximal to the cell source reservoir at the second end 1491 of the recirculation loop 1485.

FIG. 14F illustrates some of the same components of FIG. 14E. In FIG. 14F, apparatus 1486 includes resistors 1486-1, 1486-2, and an orthogonal resistor 1486-5. Additionally, apparatus 1486 includes sensors 1488-1, 1488-2, 1488-3, and 1488-4. As such, the pressure wave may be generated using resistor 1486-1, and/or resistor 1486-5, and sensors 1488-1, 1488-2, 1488-3, and 1488-4 may help to identify the location of the cell within the recirculation loop 1485.

FIG. 14G illustrates some of the same components of FIG. 14F. In FIG. 14G, apparatus 1487 includes resistors 1486-1, 1486-2, and 1486-6, and an orthogonal resistor 1486-4. Additionally, apparatus 1486 includes sensors 1488-1, 1488-2, 1488-3, and 1488-4. As such, the pressure wave may be generated using resistor 1486-1, 1486-4, and/or resistor 1486-6, and sensors 1488-1, 1488-2, 1488-3, and 1488-4 may help to identify the location of the cell within the recirculation loop 1485. Additionally, apparatus 1487 is lacking nozzle 1487 and resistor 1486-3, such that cells move from the cell reservoir, through the recirculation loop 1485, and back into the cell reservoir.

Additionally, FIG. 14H illustrates some of the same components of FIG. 14G. In FIG. 14H, apparatus 1488 includes resistors 1486-1, and 1486-6, as well as sensors 1488-1, 1488-2, 1488-3, and 1488-4. As such, the pressure wave may be generated using resistor 1486-1, and/or resistor 1486-6, and sensors 1488-1, 1488-2, 1488-3, and 1488-4 may help to identify the location of the cell within the recirculation loop 1485. Additionally, apparatus 1488 includes nozzle 1487 and resistor 1486-3 disposed on end 1491 of the recirculation loop 1485, such that cells may move from the cell reservoir, through the recirculation loop 1485, and back into the cell reservoir, or from the cell reservoir, through the recirculation loop 1485, and eject out nozzle 1487 by firing resistor 1486-3. To further assist in the movement of cells through the recirculation loop 1485 to either the cell reservoir or to nozzle 1487, resistor 1486-7 is also disposed within the recirculation loop 1485.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A method, comprising:

moving a cell of a sample into a cell probing chamber of a microfluidic device;

while the cell is in the cell probing chamber, generating a pressure wave within the cell probing chamber by actuating a fluidic pump;

acquiring, using an imaging array, a plurality of images of the cell, wherein the imaging array is synchronized with each actuation of the fluidic pump such that the plurality of images are acquired before, during, and after each pressure wave is applied; and determining a deformability of the cell responsive to the pressure wave, based on the images acquired in synchronization with the actuation of the fluidic pump.

2. The method of claim 1, wherein the fluidic pump includes a plurality of resistors disposed within the cell probing chamber, the method further including:

moving the cell into the cell probing chamber by actuating a resistor of the plurality of resistors.

3. The method of claim 1, wherein the fluidic pump includes a plurality of resistors disposed within the cell probing chamber, the method further including:

using a controller communicatively coupled to the plurality of resistors, selectively actuating a resistor of the plurality of resistors, or the plurality of resistors, to position the cell between the plurality of resistors.

4. The method of claim 1, wherein the fluidic pump includes a plurality of resistors disposed within the cell probing chamber, and wherein generating the pressure wave includes actuating the plurality of resistors at a specified frequency to generate a steam bubble at each respective resistor, each steam bubble forming at the specified frequency.

5. The method of claim 1, including determining the deformability of the cell using a high speed imaging array or a stroboscopic imaging array.

6. The method of claim 1, including:

generating a plurality of pressure waves within the cell probing chamber by actuating the fluidic pump, wherein each of the plurality of pressure waves provides a step-wise application of pressure on the cell.

7. The method of claim 1, wherein generating the pressure wave comprises:

while the cell is the only cell in the cell probing chamber, generating a discrete and time-controlled pressure wave within the cell probing chamber by actuating the fluidic pump.

\* \* \* \* \*